(12) United States Patent
Dämmig et al.

(10) Patent No.: US 7,103,440 B2
(45) Date of Patent: Sep. 5, 2006

(54) USE OF MICROWAVES FOR SENSORS IN THE SPINNING INDUSTRY

(75) Inventors: Joachim Dämmig, Ingolstadt (DE); Chokri Cherif, Ingolstadt (DE)

(73) Assignee: Rieter Ingolstadt Spinnereimaschinenbau AG, Ingolstadt (DE)

( * ) Notice: Subject to any disclaimer, the term of this patent is extended or adjusted under 35 U.S.C. 154(b) by 525 days.

(21) Appl. No.: 10/283,011

(22) Filed: Oct. 29, 2002

(65) Prior Publication Data

US 2003/0150266 A1 Aug. 14, 2003

(30) Foreign Application Priority Data

Dec. 11, 2001 (DE) .................. 101 60 757
Feb. 1, 2002 (DE) .................. 102 04 328

(51) Int. Cl.
    *G01G 7/00* (2006.01)
(52) U.S. Cl. .................. 700/143; 19/239
(58) Field of Classification Search .................. 19/236, 19/238, 239, 240, 258, 98, 105, 300; 57/412; 700/130, 142, 143; 702/170, 172; 324/634, 324/635, 644, 699, 633
See application file for complete search history.

(56) References Cited

U.S. PATENT DOCUMENTS

| | | | |
|---|---|---|---|
| 2,942,303 A | 6/1960 | Bossen et al. | |
| 4,653,153 A * | 3/1987 | Felix et al. .................. 19/240 |
| 4,809,405 A | 3/1989 | Brüderlin et al. | |
| 4,864,853 A | 9/1989 | Grunder et al. | |
| 4,885,527 A | 12/1989 | Lacombe et al. | |
| 4,887,155 A | 12/1989 | Massen | |
| 4,949,431 A | 8/1990 | Gasser | |
| 5,397,993 A | 3/1995 | Tews et al. | |
| 5,429,246 A | 7/1995 | Kaiser et al. | |
| 5,501,100 A | 3/1996 | Baechler et al. | |
| 5,509,179 A | 4/1996 | Mondini et al. | |
| 5,630,251 A | 5/1997 | Leifeld | |
| 5,697,247 A | 12/1997 | Zehr | |
| 5,796,220 A | 8/1998 | Clapp et al. | |
| 5,815,889 A | 10/1998 | Barth et al. | |
| 5,815,890 A | 10/1998 | Leifeld | |
| 5,926,267 A | 7/1999 | Farber | |
| 5,943,740 A | 8/1999 | Slavik et al. | |
| 6,081,972 A * | 7/2000 | Strobel et al. .................. 19/239 |
| 6,088,094 A | 7/2000 | Chu et al. | |
| 6,088,882 A | 7/2000 | Leifeld | |

(Continued)

FOREIGN PATENT DOCUMENTS

DE 4005548 A1 8/1991

(Continued)

OTHER PUBLICATIONS

German Patent Office Search Report, May 7, 2002.

(Continued)

*Primary Examiner*—Danny Worrell
(74) *Attorney, Agent, or Firm*—Dority & Manning

(57) ABSTRACT

The invention uses microwaves in the spinning industry in order to determine the band mass of an elongated, substantially non-twisted fiber structure. In addition, a method for measuring the sliver mass from the frequency detuning and the damping of resonance signals of a microwave sensor while taking into consideration the moisture of the fiber structure with a computer is suggested. Likewise, a corresponding spinning preparation machine and a laboratory device for measuring the sliver mass are part of the invention. Lastly, a method and a spinning preparation machine for recognizing foreign matter in a moved fiber structure with the aid of microwaves is suggested.

53 Claims, 3 Drawing Sheets

U.S. PATENT DOCUMENTS

| | | |
|---|---|---|
| 6,119,312 A | 9/2000 | Leifeld |
| 6,119,313 A | 9/2000 | Gohler |
| 6,286,188 B1 | 9/2001 | Muller et al. |
| 6,417,676 B1 | 7/2002 | Schröder et al. |
| 6,476,619 B1 * | 11/2002 | Moshe et al. ............... 324/634 |
| 6,499,194 B1 * | 12/2002 | Gresser et al. ................ 19/239 |
| 6,581,248 B1 * | 6/2003 | Muller et al. ................ 19/239 |
| 6,837,122 B1 | 1/2005 | Hermann et al. |
| 2001/0000946 A1 | 5/2001 | Moeller |
| 2002/0149378 A1 | 10/2002 | Schroder |
| 2004/0194257 A1 | 10/2004 | Dammig et al. |

FOREIGN PATENT DOCUMENTS

| | | | |
|---|---|---|---|
| DE | 4034333 A1 | 12/1991 |
| DE | 4332347 A1 | 3/1995 |
| DE | 4445720 A1 | 6/1996 |
| EP | 0340756 B1 | 11/1989 |
| EP | 0468057 A1 | 1/1992 |
| EP | 0799419 B1 | 10/1997 |
| WO | 0012974 | 3/2000 |
| WO | 0055606 | 9/2000 |

OTHER PUBLICATIONS

Patent Abstract Of Japan No. 63210757, Sep. 1, 1988.

EPO Search Report, Jun. 17, 2003.

* cited by examiner

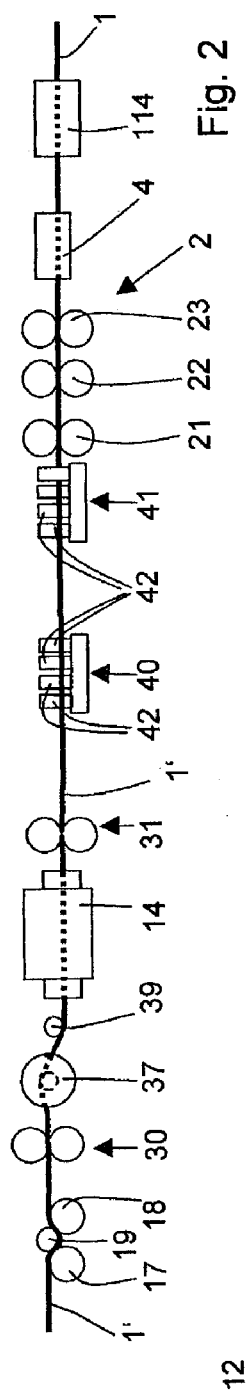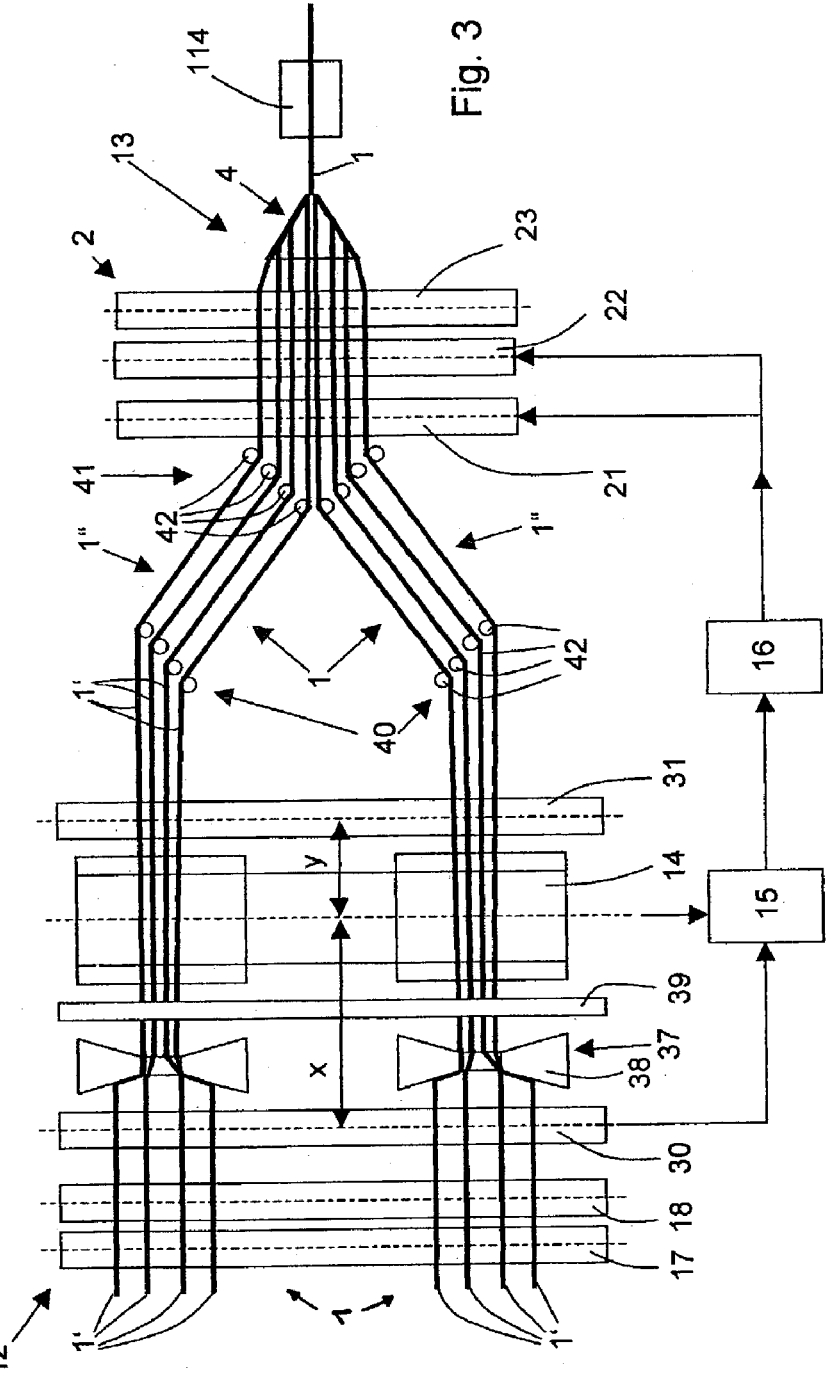

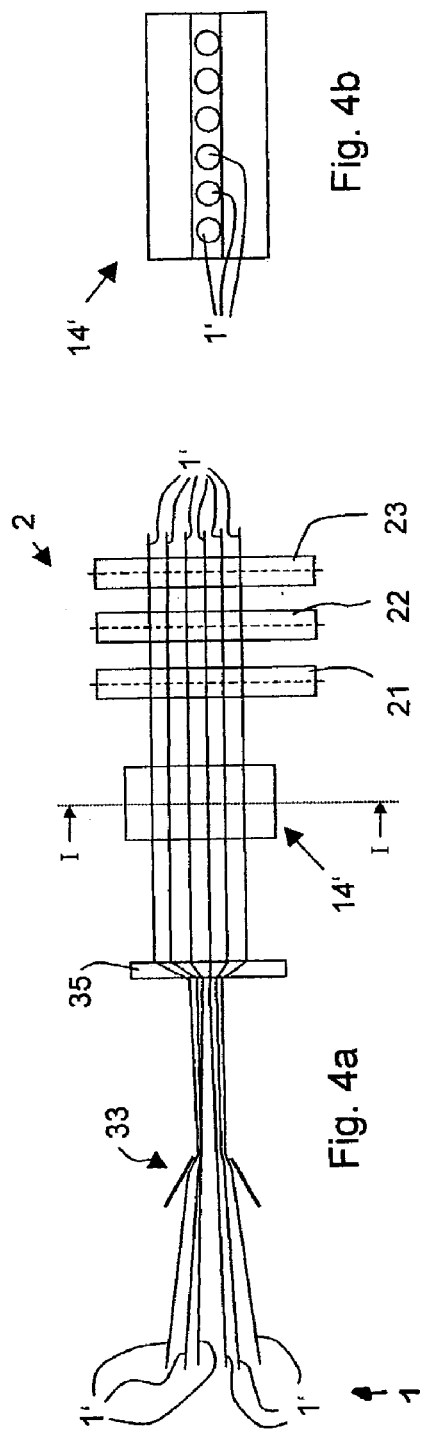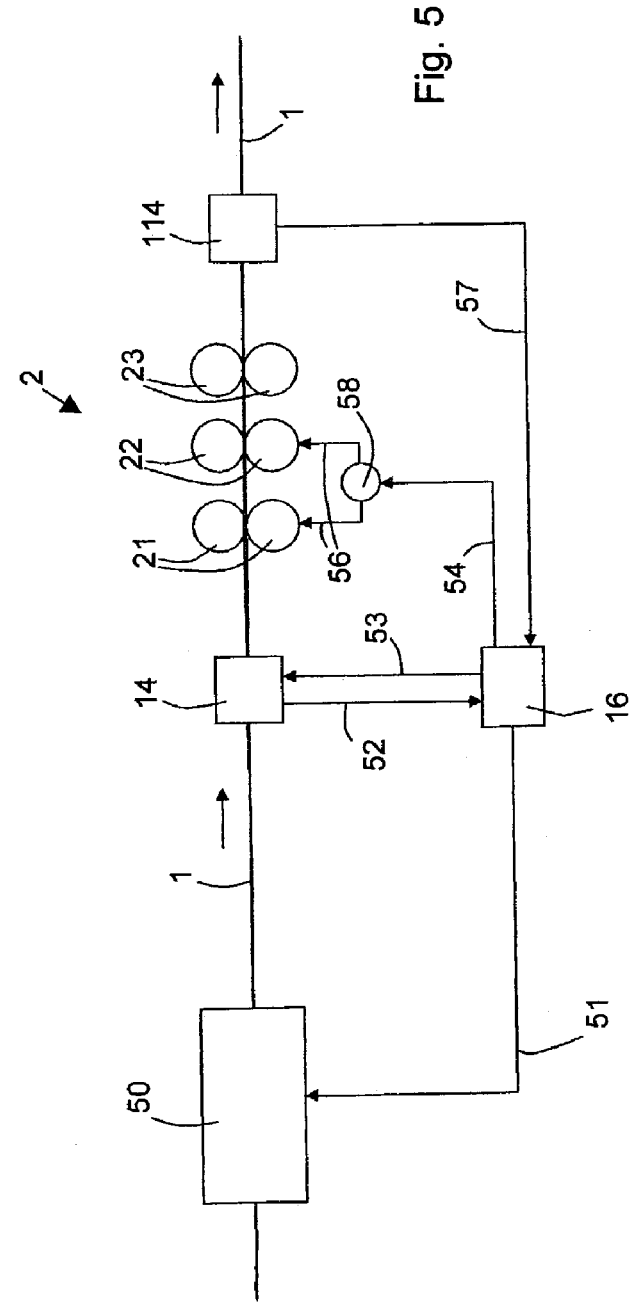

USE OF MICROWAVES FOR SENSORS IN THE SPINNING INDUSTRY

BACKGROUND

The invention is relative to the use of microwaves in the spinning industry. The invention is also relative to a method for determining the band (fiber band, sliver, slubbing) mass (bulk) of a moved fiber structure in a spinning preparation machine. The invention is furthermore relative to a corresponding machine preparation machine and to a corresponding measuring device. The invention is also relative to the recognition of foreign matter in a textile fiber structure by means of microwaves.

In the spinning industry, an evened-out fiber structure is first produced, e.g., from cotton, in several process steps and finally a twisted yarn is produced as the final product. The spinning preparation machines such as cards [carding machines] and draw [drawing] frames, that are arranged in front of the yarn production, have the particular task of stabilizing (leveling out) the fluctuations in sliver mass of one or several slivers or fiber bands, designated in the following in a summarizing manner as fiber structure. To this end, e.g., sliver sensors are arranged on draw frames, which sensors measure the sliver mass or fluctuations in sliver mass and transmit this information to a regulating unit that appropriately regulates at least one of the drawing members of the drafting device. A draw frame that operates in accordance with such a regulating principle is, e.g., the RSB-D30 model of the RIETER company. Information about the fluctuations of sliver mass is desired in many instances even in unregulated draw frames. An appropriate sensor at the outlet of such a draw frame emits, e.g., an appropriate cutoff signal for the machine and/or a warning signal if a threshold value of the sliver mass is exceeded or dropped below.

In order to measure the sliver mass and fluctuations of sliver mass (band), mechanical scanning devices in particular are known that are used today in almost all appropriate machines. However, the dynamics of these mechanical sensors is no longer sufficient at delivery speeds of more than 1000 m/min. In addition, the necessary, strong mechanical compression in front of the mechanical sensor has a noticeably negative effect on the drawing capacity.

In addition to the mechanical scanning of the fluctuations of sliver mass, other scanning principles have been suggested. Thus, e.g., U.S. Pat. No. 2,942,303 and DE 44 45 720 A1 teach measuring the sliver thickness in a contactless manner with penetrating optical radiation. However, the precision of measuring in this instance is heavily influenced by the ambient influences, e.g., temperature, moisture and dirt. Moreover, the method is susceptible to dye and reflection properties of the fiber structure.

Other known contactless measuring methods are those that use ultrasound waves. Measuring methods that operate capacitively or pneumatically are also known. The use of X-rays or γ-rays has also been suggested. However, all these methods are sensitive to moisture. It is therefore not very useful that climatic influences such as the temperature and the relative atmospheric moisture can be compensated as a rule in order to minimize climatic influences. The problem of inherent yarn moisture can not be readily eliminated in this manner. It is only mentioned here that viscose has a moisture of approximately 13%, e.g., at 40% relative atmospheric moisture. At a relative atmospheric moisture of 90% this value rises to 25%. In addition, the yarn moisture can vary by up to 5% under steady ambient conditions in one and the same batch of cotton. Also, the upper cotton layers in a can delivered to a spinning preparation machine absorb more moisture than the layers under them. Moreover, the textile fibers absorb differing moisture due to the change of climatic conditions in a spinning mill—e.g., mornings vs. afternoons vs. evenings. The cited influences, for their part, greatly influence the measured result of the sliver mass and therewith the quality of regulation.

The invention has the problem of improving the substantially contactless determination of the band mass of a fiber structure and, in general, measurements on a fiber structure.

SUMMARY

Objects and advantages of the invention will be set forth in part in the following description, or may be obvious from the description, or may be learned through practice of the invention.

The problems noted above are solved by using microwaves to determine the band mass of an elongated, substantially non-twisted fiber structure. Likewise, the problem is solved in a method wherein the band mass of a moved fiber structure in a spinning preparation machine with several successive draw parts for drawing the fiber structure is characterized in that the method comprises the following steps:

Microwaves are coupled into at least one resonator of a microwave sensor with variable self resonance, The fiber structure is guided through or along the at least one resonator in such a manner that the self resonance varies on account of the varying band mass and moisture of the fiber structure, The microwave frequency is adapted by processor-controlled coordination to the self resonance, The frequency-adapted microwaves coupled out of the at least one resonator are detected as regards frequency detuning and damping, The band mass is calculated from the frequency detuning and the damping with the aid of a processor, taking into account the moisture of the fiber structure by calculation [with a computer].

As regards a spinning preparation machine according to the invention, especially a card, draw frame or combing machine, the machine is provided with at least one sensor for measuring the band mass of continuously moved fiber structure, which at least one sensor comprises:

At least one microwave generator for producing microwaves of processor-controlled, variable frequencies, At least one microwave resonator into which the microwaves of variable frequency can be coupled, A specimen volume for receiving the fiber structure as part of the microwave resonator, a detector for detecting microwaves coupled out of the resonator and An evaluation unit for evaluating the microwave resonance signals as regards the band mass of the fiber structure, with computer-aided consideration of the fiber structure moisture.

The problem is also solved by a laboratory device including at least one microwave generator for generating microwaves of processor-controlled, variable frequencies, with at least one microwave resonator into which the microwaves of variable frequency can be coupled, with a specimen volume for receiving the fiber structure as part of the microwave resonator, with a detector for detecting microwaves coupled out of the resonator, and with an evaluation unit for evaluating the microwave resonance signals as regards the band mass of the fiber structure while taking the fiber structure moisture into consideration with a computer.

As concerns the recognition of foreign matter, the problem is solved by a method for recognizing foreign matter in a moved fiber structure in a spinning preparation machine, characterized in that the method comprises the following steps:

Microwaves are coupled into at least one resonator of a microwave sensor with variable self resonance, The fiber structure is guided through or along the at least one resonator in such a manner that the self resonance varies on account of the presence of foreign matter in the fiber structure, The microwave frequency is adapted by processor-controlled coordination to the self resonance, The microwaves coupled out of the at least one resonator and adapted in frequency are detected as regards frequency detuning and damping, The band mass is calculated from the frequency detuning and the damping with the aid of a processor and the presence of foreign matter is also calculated.

The invention suggests for the first time the use of microwaves in the spinning industry in order to measure the band mass of a substantially non-twisted fiber structure and to perform recognition of foreign matter. A possible use of microwaves for this purpose was not known previously even though microwaves have long been known for the measuring of material properties.

When the measuring of the sliver mass is discussed in the framework of this invention, this formulation also includes the measuring of equivalent magnitudes such as, in particular, the substance cross-section or the sliver density or the fluctuations of these magnitudes.

The invention is especially suited for measuring textile yarn strands that are substantially non-twisted, that is, twisted at the most only to an extremely slight extent, such as, e.g., cotton strands that are delivered to a spinning preparation machine or that leave the machine. Other natural and synthetic fiber types can also be measured as well as mixtures of natural and synthetic fibers.

The use of microwaves in accordance with the invention can be realized, e.g., in that an elongated fiber structure with a fiber moisture is introduced into a specimen volume that is part of at least one microwave resonator. Microwaves are generated by at least one microwave generator and coupled into the resonator, that operates either according to the reflection principle or the transmission principle. The resonance frequency, that is, the self resonance, changes in comparison to the empty resonator based on the presence of the moist fiber structure. The new resonance frequency can be determined and adjusted by a processor, during which the damping of the signal of the decoupled microwaves is also measured in addition to this resonance frequency with the aid of an appropriately designed detector. Using the measured signals for the new self resonance, the fiber moisture can then be eliminated by calculation with known methods.

A possible method for evaluating the microwave signals when determining the moisture-independent measurement of density and of mass is known, e.g., from EP 0468023 B1, that is relative, however, substantially to the measuring of the density-independent, absolute moisture of cloths. The method described in the publication can be transferred in its basic features to the moisture-independent determination of the band mass or band density of a fiber structure. The disclosed content of EP 0,468,023 B1 is expressly included therewith herewith.

In the method described in EP 0,468,023 B1 a measuring curve that is substantially a function of the sliver mass and of the fiber moisture is obtained containing information about the detuned resonance frequency and the half-width. The method is based essentially on connecting the measured signal dependent of the material moisture to primary measured magnitudes such as the half-width and the resonance frequency. The measured signal is then compared to a stored calibration curve specific for the fiber material. Taking into consideration the half-width and the resonance frequency of the microwave signal with an empty resonator (without material to be measured), either the density-independent moisture or the moisture-independent density of the material to be measured can then be determined. The latter is especially interesting for the present invention.

Another, somewhat more complex method is described in DE 197 05 260 A1 and in DE 197 34 978 A1, especially for cigarette strands in which the irradiating with microwaves of two frequencies is described. The disclosed contents of these two publications is also explicitly included herewith.

The use of microwaves in accordance with the invention can be applied with preference to the determining of the band mass of a fiber structure, taking the fiber moisture into consideration. The band mass is advantageously determined in a moisture-independent manner, preferably in that the fiber moisture is eliminated by calculation when determining the band mass. Alternatively, a start can also be made from a constant, base fiber moisture, assuming, e.g., the type of fiber to be measured and fixed ambient conditions as a reference. Likewise, other parameters for the assuming of a certain base fiber moisture can be selected. Thus, e.g., the cover layers of the fiber material to be processed can be used as reference. Then, starting from the base fiber moisture, the deviations of the band mass can be determined. This method accordingly corresponds to a relative consideration of the fiber moisture of the fiber structure.

The microwave measuring principle is used with particular preference in regulating draw frames. The determined values for the sliver mass and/or the fluctuations of sliver mass are supplied to a regulating unit that correspondingly controls a draft member of a spinning preparation machine that evens out a fiber structure continuously running through it. For example, the fiber structure is drawn in a drawing device of a draw frame in a preliminary draft zone and in a following main draft zone. Each draft zone is formed by two roller pairs and the fiber structure is clamped between the rollers of such a clamping roller pair. The circumferential speeds of the rollers of the individual roller pairs increase in the direction of draw. A controlling, e.g., of the entrance roller pair and of the middle roller pair of three successive roller pairs alters their circumferential speed and thus also the draft. Fluctuations of sliver mass and of sliver thickness can be regulated out in this manner.

The invention can also be used with advantage in cards. Here, e.g., the replacement of the path measuring sensor usually used in the feeler rollers (one of the two feeler or draw-off rollers can be radially deflected, which deflection is a measure of the sliver thickness) with the at least one microwave sensor is advantageous. The draft members of the card can then be correspondingly regulated. Alternatively or additionally, a regulating of the card feed is possible.

The use in accordance with the invention is also provided in the case of regulated cards comprising a regulated drafting device at the output for the fiber structure, that is then designated as a fiber fleece, or in the case of draw frames. Likewise, the invention can be used in combing machines with a regulated drafting device arranged at the output. An unregulated drafting device can be optionally arranged in front of this regulated drafting device. In cards and combing machines, the drafting device can be advantageously delivered in the form of a module to the output of these spinning preparation machines. The designation "module" signifies that the card or combing machine on the one hand and the drafting device on the other hand do not form an entire, uniform machine but rather a machine compound. An appropriate adaptation to one another is necessary.

The microwave measuring technology in accordance with the invention can also be used with advantage in laboratory devices in which a section separated out of the entire fiber structure is measured. Likewise, a portable device can be used with advantage solely for temporary measurements in spinning preparation machines. This device can then be used as needed, in various spinning preparation machines, e.g., in unregulated draw frames such as, e.g., the non-regulated SB-D 10 of the Rieter company, in order to perform certain basic adjustments to the machine. This includes, e.g., the nip line interval between two roller pairs, the preliminary draft, the delivery speed of the drawn fiber structure, the position of a pressure rod in a draft zone, and similar adjustments.

In principle, the invention can be used in particular at the inlet and/or outlet of a drafting device of a spinning preparation machine. If the microwave sensor is used at the inlet of the spinning preparation machine and the measured values or the results of the evaluation of the measured values fed to the regulation, this is called an inlet regulation. If the microwave sensor is used at the machine outlet, it is an outlet regulation. In particular, long-wave, re-occurring fluctuations of sliver mass can be regulated out with the latter. A combination of inlet regulation and of outlet regulation is also advantageous and forms a so-called meshed regulation. DE 0,176,661 A2 describes an example, the disclosed content of which is explicitly included herewith.

It is also advantageous to carry out a plausibility check for a mechanical sensor at the outlet by means of a microwave sensor at the outlet of the spinning preparation machine. In other words, the mechanical sensor is checked with the aid of the microwave sensor so that, e.g., when a pre-selected A % limit value is attained (long-wave fluctuations of sliver), an automatic correction of the machine adjustment values or a laboratory check of the defectively drawn fiber structure is performed in order to subsequently manually adjust the machine—e.g., the nip line intervals of drafting device rollers—appropriately.

As an alternative or addition to a stabilizing (leveling out) of the fluctuations of band mass, the invention can also be used to monitor the fiber structure running in and/or out. Then, e.g., the quality of the mechanical adjustments can be determined in particular in unregulated draw frames as a function of various fiber materials with the aid of the microwave sensor. Likewise, a turning off of the machine and/or the emitting of a warning signal if a threshold value of the band mass of the exiting fiber structure is exceeded or dropped below can be realized.

The microwave measuring technology can also be used as a monitoring member for detecting a band break. Such a monitoring can take place, e.g., at the inlet of a draw frame, e.g., by measuring the fiber structure over a certain number of periods, during which the machine cuts off if a given threshold value is dropped below. Such a monitoring is also possible at the outlet of the draw frame or in other spinning preparation machines. The at least one microwave sensor advantageously assumes the detection of sliver mass and also the detection of a sliver break, since even in the latter instance a threshold value for the band mass is dropped below.

It is advantageous if, in addition to the sliver mass, the sliver moisture and/or the sliver temperature is detected, that is measured, e.g., by IR rays in the appropriate sections. Even these magnitudes can then be used to control the machine. A high sliver moisture, that can occur especially frequently in the case of cover layers of slivers drawn out of spinning cans, influences the draft behavior to a relatively great extent. Also, the formation of windings can be a consequence of too high sliver moisture. It is therefore advantageous to also include the sliver moisture in the control/regulation of the draw part. The same applies to the sliver temperature.

It is especially preferable if the measuring frequency with which the microwave resonance signals adapted in the resonance frequency are coupled out or processed is coordinated with the run-in speed of the fiber structure running into the spinning preparation machine. Alternatively, the measuring frequency is coordinated with the delivery speed of the fiber structure leaving the machine. In other words, a machine-synchronous measuring frequency is adjusted. This means that fixed scanned lengths, e.g., 1.5 mm, are maintained independently of the sliver speed. This length-oriented scanning at given intervals along the fiber structure (constant interval length) hinders in particular surges and simplifies the evaluation of the measured results. In order to realize this variable measuring and/or scanning frequency an external synchronization input can be provided in the detector, that receives synchronization signals from the sliver speed.

An alternative method is a time-oriented scanning in which the measuring frequency is a function of the sliver speed. This approach corresponds to the length-oriented scanning, only another reference system is selected.

In order to compensate a possibly too coarse resolution of the measuring method, the measurements along the sliver are preferably carried out in several successive, locally overlapping measuring sections. If the resolution is, e.g., 1 cm, the measuring frequency is selected in such a manner, e.g., that a new measurement is performed every 2 mm along the sliver. Thus, 1 cm of sliver length is scanned in five steps. In other words, successive measurements are carried out staggered relative to each other each 2 mm in the direction of the sliver so that each 2 mm long fiber structure section is detected five times. Such an overlapping of measured values reduces the integration length and increases the effective resolution by mathematical calculations. The real resolution of each measurement remains unchanged thereby, that is, at 1 cm in the example given above.

The cited method for increasing the effective resolution is preferably used at the outlet of the draw frame. Previously, spectrograms of sliver below approximately 1 cm or even below 10 cm leaving the draw frame were interpolated since the dynamics of the mechanical scanning devices used is too low. Therefore, a real measured CV value at 1 cm and less is very interesting. Therefore, a spectrogram of the fiber structure is recorded with the aid of the at least one microwave sensor or a part of such a spectrogram supplemented, preferably at least in the very short-wave range, especially also at the inlet and/or outlet of the spinning preparation machine.

It is especially preferable if the fiber structure is guided substantially without oscillations through the at least one resonator. In this manner falsifications of the measured values can be avoided. An advantageous possibility for realizing such a freedom from oscillations or of reducing them is realized by a lateral guiding, that is, transversally to the fiber structure. The fiber structure is either guided only from one side or from several sides (this is a contactless measuring principle in spite of such a guidance).

The fiber structure preferably runs through the at least one resonator under tension in the longitudinal direction, advantageously with a slight force of tension so that the fiber structure does not become distorted thereby. Such a tension is preferably realized by guide means in front of and behind the at least one resonator. The guide means can preferably also assume an alignment of the slivers in the transverse direction of the slivers.

Guide means for guiding and/or tensioning can advantageously be realized by a pair of transport rollers clamping the sliver in front of and behind the at least one resonator, which rollers are preferably undulated in order to improve the clamping action.

Alternatively or additionally, a funnel that is open in the circumferential direction or closed is located in front of the at least one resonator by which funnel the sliver or a group of slivers, in which instance several groups form the fiber structure, is compressed and guided in the transverse direction. Instead of a funnel, e.g., guide sheets, guide rods or the like can be used.

Alternatively or additionally, the sliver or individual groups of slivers forming the fiber structure is/are guided in front of the at least one resonator via a guide means designed as a compressing element with guide surfaces rising transversely to the longitudinal direction of the fiber structures. Thus, the slivers slide toward the middle and are compressed. Such a guide means is preferably designed substantially as a double cone with tips facing into one another and merging into one another and thus constitutes a guide roller. In addition, such a guide means can be designed to be rotatable in order to simplify a transport of the fiber structure in the longitudinal direction of the fiber.

Preferably at least one pressure rod running in the transverse direction of the fiber structure is arranged as an alternative or additional guide means in front of the at least one resonator. Such a guide rod is advantageously located after the previously described guide roller before the fiber structure enters into the resonator.

In other embodiments, the desired tension can also be realized with the cooperation of the drafting device rollers. If the sensor is arranged, e.g., immediately in front of the drafting device, the inlet roller pair of the drafting device, which pair is located after the sensor, can bring about the tension in cooperation with, e.g., a pair of transport rollers in front of the sensor. For the rest, an arrangement of the sensor at a short interval in front of the drafting device is preferable since the textile material to be drawn, in contrast to the state of the art when sensing with, e.g., mechanical sensing rollers, does not have to be compressed beforehand and therefore also does not have to be spread out again over a rather long path stretch to the drafting device.

If, on the other hand, the sensor is located after the drafting device, on the one hand the delivery roller pair of the drafting device located in front of it and on the other hand a calendar roller pair located after it can assure the tensioning of the drawn fiber structure.

The fiber structure is preferably guided in at least two groups through one or several resonators spaced in the transverse direction. To this end the slivers can run in either at the inlet of the spinning preparation machine already, preferably when being drawn out of spinning cans located in front of the machine, in at least two spatially separated groups, or the fiber structure is separated before running through the at least one resonator into the at least two groups. Such a division of the fiber structure can possibly increase the precision of measuring of the microwave sensor since only a part of the fiber structure runs through a specimen volume of the at least one resonator at a time.

The cited at least two groups of slivers are preferably guided onto each other after having run through the at least one resonator in order to subsequently run into a drafting device of the spinning preparation machine, in which they are drawn preferably substantially parallel to each other.

In order to prevent a relative movement between slivers in the at least one resonator that would result in the transmission of falsified information to the regulating unit and therewith in erroneous drafts, the slivers are preferably appropriately guided. For this, deflection elements are advantageously provided that are positioned in such a manner that the path stretches from the resonator to the drafting device, through which path stretches corresponding sections of different slivers run, are substantially equally long. To this end, at least two deflection elements are advantageously provided for each sliver which elements are arranged staggered relative to each other in the longitudinal and the transverse direction of the fiber structures. In this manner the length of each path stretch for the individual slivers can be adjusted to the same measure.

Furthermore, the deflection elements are preferably designed to be rotatable in order to reduce the friction between slivers and deflection elements.

In a preferred embodiment the slivers are guided adjacent to each other and running in parallel through the at least one microwave sensor. The slivers can have a substantially constant interval from each other or can also contact each other. A division into two or more groups of slivers is eliminated in this instance. This realizes, among other things, a microwave sensor that is simple in design. Such a guidance of the slivers has the advantage that they are distributed homogeneously in the resonator space (chamber). In order to realize such a homogeneous distribution of the slivers in the resonator or in the resonator space the delivered slivers can be compressed and/or spread out during the delivery, depending on the spatial arrangement.

In another embodiment of the invention, the slivers are guided not only in the resonator, but also from the inlet to the outlet adjacent to each other and, viewed from the top, running substantially in parallel through the spinning preparation machine. This prevents in particular frictional losses of the slivers due to deflection and compression.

It is advantageous if the material at least of the specimen-volume section that makes contact with the fiber structure is designed to be substantially wear-resistant in order to obtain precise measured results over a long time period and to assure a long service life of the sensor.

Since fibers can always come loose from the fiber structure again and again (fiber fly), it is purposeful to clean the specimen volume through which the fiber structure passes at intervals of time. It is especially advantageous to use compressed air or a vacuum for this purpose, that act on the specimen volume.

Alternatively or additionally, at least the specimen volume of the at least one resonator is designed so that it can shift, e.g., be moved in the transverse direction of the fiber structure during a standstill of the fiber structure in order to realize easier accessibility for an automatic or manual cleaning of the specimen volume in a cleaning position of the at least one resonator.

Advantageous further developments are characterized by the features of the subclaims.

BRIEF DESCRIPTION OF THE DRAWINGS

Exemplary embodiments of the invention are explained in the following with reference made to the figures.

FIG. 2 shows a schematic lateral view of a second embodiment of a draw frame.

FIG. 3 shows the draw frame of FIG. 2 in a top view.

FIG. 4a shows a section of a third embodiment of a draw frame in a top view with six slivers.

FIG. 4b shows a view along section I—I in FIG. 4a.

FIG. 5 shows a schematic presentation of a combination of a card or combing machine with a drafting device.

DETAILED DESCRIPTION

Figure 1:
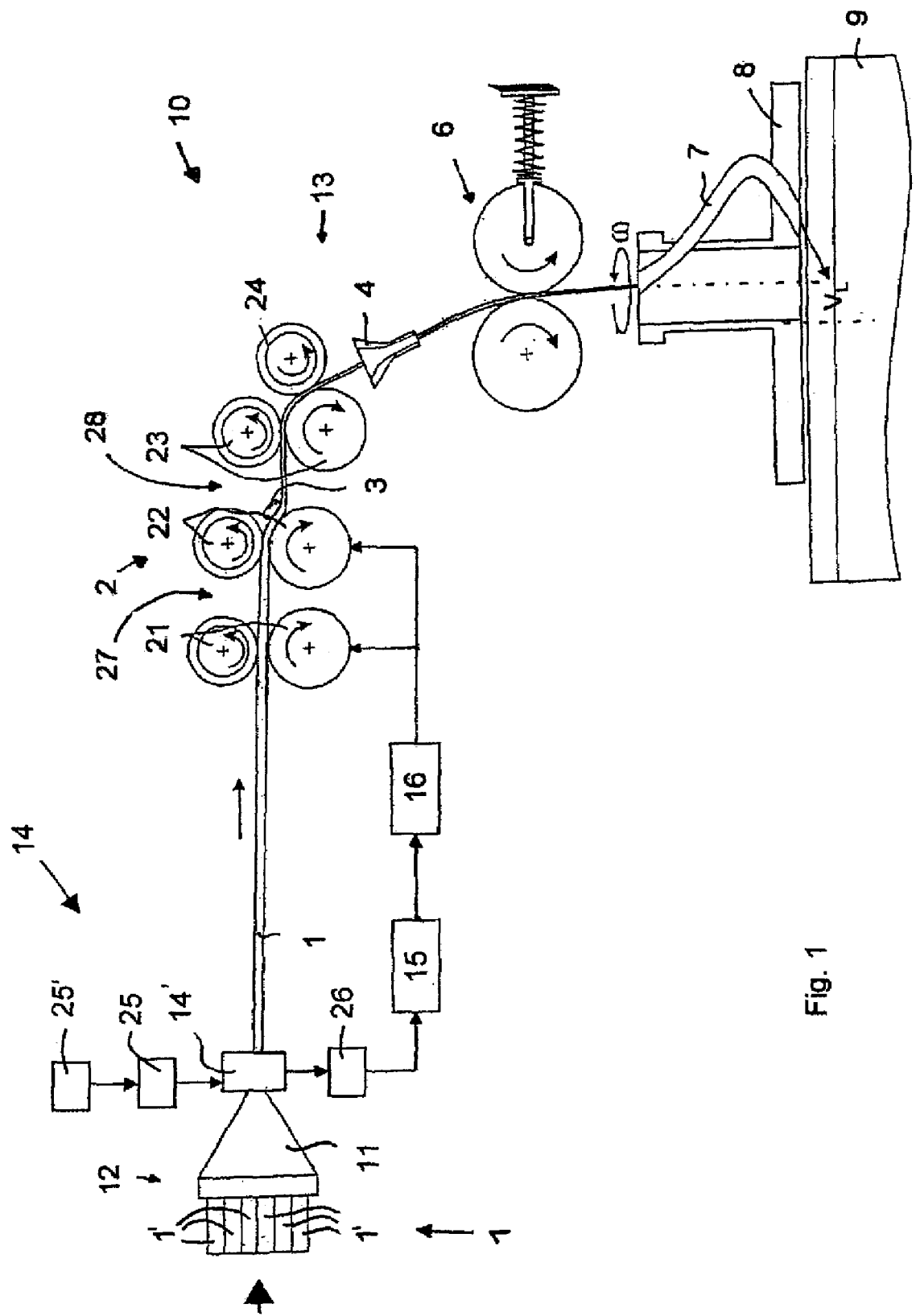
FIG. 1 shows a first embodiment of a draw frame for drawing a fiber structure.

Reference will now be made in detail to the presently preferred embodiments of the invention, one or more examples of which are show in the figures. Each example is provided to explain the invention, and not as a limitation of the invention. In fact, features illustrated or described as part of one embodiment can be used with another embodiment to yield still a further embodiment. It is intended that the present invention cover such modifications and variations.

The basic operation of a draw frame 10, as an example of a spinning preparation machine, is explained in the following using FIG. 1. According to this example several substantially non-twisted slivers 1' of draw frame 10 are placed adjacent to one another. It is also possible to deliver only one sliver 1' to draw frame 10. In both instances the term "fiber structure" is used in the scope of this invention for the placed fiber material and has the reference numeral 1 in the following.

Funnel 11, that compresses slivers 1' or fiber structure 1, is arranged at the inlet of draw frame 10. Alternatively, other compression devices can be used. It is also conceivable that compression is entirely eliminated. After having passed through a scanning device described further below or through a sensor, fiber structure 1 is guided into drafting device 2 forming the core of draw frame 10. Customary drafting devices generally comprise a preliminary draft zone and a main draft zone. In unregulated draw frames both the preliminary draft and the main draft are constant during the draft procedure. In contrast thereto, in regulated draw frames a stabilization (leveling out) takes place by altering the draft height. In a regulated drafting device, both the preliminary as well as the main draft could be altered; however, the main draft is almost always selected. The reason is that the main draft is greater than the preliminary draft so that a more precise regulation can be performed.

Drafting device 2 generally comprises three draw parts or roller pairs between which the actual draft takes place. They are entrance roller pair 21, middle roller pair 22 and exit or also delivery roller pair 23, that rotate with a circumferential speed that increases in this sequence. As a consequence of these differing circumferential speeds of the roller pairs, fiber structure 1 is drawn in accordance with the ratio of the circumferential speeds. Entrance roller pair 21 and middle roller pair 22 form cited preliminary zone 27, and middle roller pair 22 and delivery roller pair 23 cited main draft zone 28. Usually, a pressure rod 3 is additionally attached in the main draft zone, which rod deflects fiber structure 1 consisting of the slivers and thus brings about a better guidance of the fibers, in particular of the fibers not clamped between two roller pairs (so-called floating fibers). Drawn fiber structure 1 is combined (integrated) with the aid of upper deflection roller 24 and of fleece funnel 4 and deposited via calendar roller pair 6 and (curved) sliver conduit 7, that is arranged in rotary plate 8 rotating at an angular speed $\omega$, at a speed of $V_L$ into can 9.

In order to compensate for the fluctuations of sliver mass in regulated drafting devices, the placed slivers customarily run through sensor 14 located in front of drafting device 2, which sensor continuously registers the sliver thickness and forwards it in the form of electric voltage signals first to store (memory) 15, that considers the path difference and time difference between the passing of sensor 14 and the entrance into drafting device 2 (FIFO store=first-in first-out store) and then, after the passage of this time difference, forwards it to evaluation and regulation unit 16. The measured signal is accordingly stored temporarily in store 15 in order that evaluation and regulation unit 16 cuts in the regulation after a given time or after a path traversed in a defined manner by fiber structure 1. This regulation compensates the fluctuations in mass by altering the circumferential speeds of middle roller pair 22 and, if necessary, of entrance roller pair 23 (see directions of arrows). This onset point is designated as the regulating onset point. The compensation of the fluctuations of mass in main draft zone 28 is achieved by altering the speed of a regulating motor (not shown) that drives entrance rollers 21 and middle rollers 22, during which the speed of the motor for driving delivery rollers 23 is maintained constant.

According to the present invention, the scanning device or sensor 14 operates with microwaves, preferably using the resonator principle. To this end, sensor 14 comprises at least one microwave generator 25 whose frequency can be variably adjusted by processor 25' and that couples microwaves into a hollow chamber or a specimen volume of at least one resonator 14' that is also part of the microwave sensor. During the scanning, fiber structure 1 runs through the specimen volume. The sections of fiber structure 1 transported through the specimen volume influence the resonator frequency and the damping thereby in accordance with their thickness and/or mass as well as their moisture, that is reflected in a change of the amplitude and of the half-width of the signal coupled out of resonator 14' and detected by an appropriately designed microwave detector 26 also forming a part of sensor 14. The band mass of the scanned section of fiber structure can then be calculated from the detected signals and the moisture of this section can be calculated out in order that the stabilizing of the fluctuations of band mass can be subsequently carried out with the aid of evaluation and regulation unit 16. In addition to the use of microwaves, the invention is also relative to the corresponding methods and corresponding devices that measure textile, substantially non-twisted fiber structures in this manner.

FIG. 2 shows a lateral view and FIG. 3 a top view of an exemplary embodiment of a spinning preparation machine in accordance with the invention in the shape of a draw frame 10. Fiber structure 1 is transported in two groups 1", each of which comprises four slivers 1' running substantially in parallel, to inlet 12 of draw frame 10, usually by drawing them out of spinning cans (not shown) placed in front of machine 10. Slivers 1' are guided in the direction of transport via two metallic delivery rollers 17, 18 arranged in succession on which several metallic load rollers 19 arranged adjacent to each other parallel to the roller axis are centrally placed (not shown in FIG. 3 for the sake of clarity). If a sliver 1' should tear, an electric contact is closed via rollers 17, 18 19 and the sliver transport is stopped.

In FIG. 3 slivers 1' are represented for the sake of clarity as solid lines, even though they would be partially covered in a top view, as, e.g., in sensor 14 or drafting device 2.

Rollers 17, 18, 19 are followed by transport roller pair 30 that is designed as a guide means and that is followed by two other guide elements spaced in the transverse direction of the slivers and of transport and designed as compression elements 37. A group 1" of four slivers 1' is guided over each compression element 37. Compression elements 37 are designed as double cones with tips facing one another and merging into one another. Slivers 1' slide off on laterally rising guide surfaces 38 and are compressed therewith.

As an alternative to compression elements 37, e.g., a funnel (not shown) can also be used that also serves to compress four slivers 1' at a time.

Compression elements 37 are followed by pressure rod 39 under which slivers 1' are guided in order to subsequently enter into the specimen volume of a resonator of microwave sensor 14. This sensor 14 comprises two specimen volumes. A sliver group 1" can be introduced, e.g., from both sides of draw frame 10 into a corresponding specimen volume of sensor 14. Other designs of sensor 14 are of course possible.

Sensor 14 is followed by another transport roller pair 31 that, in cooperation with transport roller pair 30 (as well as with compression element 37 and pressure rod 39) also serves to guide and especially to generate a tension in fiber structure 1. Oscillations of slivers 1' are avoided in particular in that the interval x of transport roller pair 30 and the interval y of transport roller pair 31 to sensor are selected to be small.

Deflection elements 42 for slivers 1' are provided downstream from transport roller pair 31 that bring slivers 1' back together. These deflection elements 42 have the particular purpose of seeing that the individual slivers 1' traverse path stretches of equal length from sensor 14 to drafting device 2. It is assured in this manner that the sliver sections measured at the same time as regards the sliver mass also run through drafting device 2 at the same time and that an exact draw can be achieved therewith. If slivers 1' would move relative to each other on their path from sensor 14 to drafting device 2, erroneous draws would be the consequence.

In the embodiment shown in FIGS. 2, 3 four deflection elements 42 at a time are combined to a group of four 40, 41 and one deflection element 42 of a group 40, 41 is provided for deflecting a sliver 1'. Deflection elements 42 of each group of four 40, 41 are arranged in alignment and running at an angle of approximately 45° to the direction of transport of the fiber structures. A total of two deflection elements 42 are provided for each sliver 1', which deflection elements are arranged in the direction of transport of the fiber structures in such a manner that they are staggered longitudinally as well as transversely so that a sliver 1' is deflected twice on its path from sensor 14 to drafting device 2. Deflection elements 42 of groups 40, 41 are arranged in such a manner thereby that the outside sliver 1' of a sliver group 1" in the upstream group of four 40 is deflected at a later point in time and in the downstream group of four 41 at an earlier point in time than the inside sliver 1'. In sum, the path stretches each sliver 1' passes through from sensor 14 to drafting device 2 are equally long.

In the embodiment of FIGS. 2, 3 deflection elements 42 are designed as vertically aligned round rods. Deflection means 42 can be designed to be rotatable about a vertical axis in order to reduce the friction for slivers 1'.

After having been deflected by deflection elements 42, slivers 1' run into drafting device 2 and are drawn. The measured signals of sensor 14 (the microwave detector is not shown) are transmitted, as previously described, via temporary store 15 to evaluation and regulation unit 16 that brings about a control of entrance and of middle roller pairs 21, 22 (run-in regulation). Drafting device 2 is followed by compressing funnel 4 and subsequently by microwave sensor 114 serving, e.g., to monitor sliver at outlet 13 of drafting device 2. This sensor 114 can be designed in particular in such a manner that it brings about a cutting off of machine 10 and/or brings about the emitting of a warning signal if drawn fiber structure 1 does not have the desired quality. A regulation of the outlet (not shown) with the aid of sensor 114 arranged on outlet 13 is also possible.

FIGS. 2, 3 show only one sensor 14, 114 (each without microwave generators and microwave detectors for the sake of clarity) in front of and behind drafting device 2. It is also possible to use several sensors 14, 114 that measure only a part of fiber structure 1 for the band mass. Thus, it is, e.g., possible that instead of sensor 14 shown in FIGS. 2, 3 with its two specimen volumes two sensors 14 are used, in which instance such a sensor measures one sliver group 1".

Likewise, it is not obligatory that slivers 1' are guided in one plane, as is especially apparent in FIG. 3. The transport cross section of slivers 1' can also be selected to be different. For example, two slivers 1' at a time can be guided through the specimen volume adjacent to one another and over one another or staggered opposite one another.

In FIG. 4a (top view) and in a small section in FIG. 4b (view in direction I—I of FIG. 4a) an alternative embodiment of a draw frame is schematically shown. Six presented slivers 1' are combined in a funnel or two guide sheets 33 tapering toward one another in the direction of sliver transport—alternatively, two guide rods may be used. Slivers 1' are widened out in such a manner by subsequent widening-out element 35 that each two slivers 1' running adjacent to one another are arranged at substantially the same interval. Widening-out element 35 is designed, e.g., as an upwardly bent round rod. In alternative variants slivers 1' are combined at a substantially constant transverse interval with, e.g., the aid of compression elements 38 in accordance with FIGS. 2, 3. It is essential here that slivers 1' run through the resonator space with a homogeneous distribution. This is illustrated in FIG. 4b: The six slivers 1' have a substantially constant interval transversely to their direction of transport. Slivers 1' can also make contact with each other. No disturbing frictional effects occur thereby at the same transport speed.

As FIG. 4a also shows, the path stretch through which slivers 1' run is short from sensor 14 to drafting device 2. On the other hand, in traditional drafting devices, that operate with mechanical sliver scanning and therefore with sliver compression, this path stretch is designed to be substantially longer since, e.g., viscose opens relatively poorly after a compression. The result is that a relatively great distance must be provided for this between the mechanical scanning (sensing) device and the drafting device. In the instance of a contactless scanning by microwaves, this interpositioning of a longer distance is not necessary, so that sensor 14 can be arranged directly in front of drafting device 2. The entire length of the machine can be distinctly reduced therewith, if necessary.

Drafting device 2 of FIG. 4a is preferably followed by a fleece funnel, a sliver funnel and, subsequently, a calendar roller pair (not shown) and another microwave sensor can be arranged between these various structural components.

FIG. 5 shows a combination of a card 50 and a subsequent, regulated drafting device 2 between which microwave sensor 14 is arranged. The measured values of sensor 14 are supplied via signal lead 52 to evaluation and regulation unit 16 (a store 15 as in FIGS. 1, 3 has been omitted) and evaluated there. Evaluation and regulation unit 16 can then initiate via signal leads 51, 54 a regulation of card 50 (regulation of the card draw parts and/or of the card feed) or a control of draw parts 21, 22 of drafting device 2, which parts 21, 22 are designed as rollers. During the controlling of drafting device 2, servomotor 58 with a differential transmission connected at the outlet side (not shown) is used via signal lead 54 to control the drive of draw parts 21, 22 via signal leads 56. The drive for draw parts 23 is not shown (as also in FIG. 1).

A second microwave sensor 114 is connected at the outlet side of drafting device 2, which sensor can not only perform a monitoring of the sliver exit but can also be used to calibrate sensor 14. To this end, signal lead 53 is provided from evaluation and regulation unit 16 to sensor 14. The two sensors 14, 114 can be adapted to one another in this manner.

Sensor 114 can also be used to regulate the draw parts of drafting device 2 in order to compensate long-wave fluctuations of sliver in particular. Together with the control based on the measured signals from sensor 14, this realizes a so-called meshed regulation.

Instead of card 50, a combing machine can be provided in its place to which a regulated drafting device is connected at the outlet side. In addition, a non-regulated drafting device (not shown) can be provided between the combing machine and the regulated drafting device. The combing machine can be regulated by evaluation and regulation unit 16, like the card, while regulated drafting device 2 is controlled and/or regulated.

The invention is also relative to the use, a corresponding method, and to a corresponding device for recognizing foreign matter in a textile fiber structure that can be present in a substantially non-twisted (fiber fleece, sliver) or twisted (as yarn) state. The principle for evaluating the microwave signals is similar here to the one presented before for the substantially non-twisted fiber structure. Foreign matter can result, as a function of the dielectric constant of the foreign matter, e.g., in a higher band mass value than the actual one. The measured signal can be characteristic for the particular foreign matter and recourse can be made, e.g., during the computer-supported evaluation of signals to stored characteristic values (e.g., in the form of a knowledge base). The foreign matter can be of metallic or organic nature. The foreign matter can be determined particularly well if its dielectric constant deviates distinctly from that of the fiber material. The fiber moisture can be taken into consideration as described earlier.

It should be apparent to those skilled in the art that various modifications and variations can be made to the embodiment of the invention described herein without departing from the scope and spirit of the invention as set forth in the appended claims and their equivalents.

The invention claimed is:

1. A method for determining band mass of an elongated, substantially non-twisted fiber structure in a textile spinning machine, comprising subjecting the fiber structure to microwaves such that a characteristic change of the microwaves is induced by the fiber structure, detecting and processing the changed microwave characteristic to calculate the band mass of the scanned fiber structure, and adjusting the band mass as a function of moisture content of the fiber structure, wherein a relatively constant base fiber moisture is assumed for the fiber structure, and the band mass is adjusted based on the assumed fiber moisture.

2. The method as in claim 1, wherein the band mass of a substantially natural fiber structure is determined.

3. The method as in claim 1, wherein the band mass of a substantially synthetic fiber structure is determined.

4. The method as in claim 1, comprising conveying the fiber structure continuously through a chamber wherein the fiber structure is scanned by the microwaves.

5. The method as in claim 1, wherein the fiber structure is scanned with the microwaves in a microwave resonator wherein microwaves of a variable frequency are coupled into the resonator such that a resonance frequency is produced as a result of density and moisture of the scanned fiber structure, the resonance frequency being detected and evaluated for determining band mass.

6. The method as in claim 5, wherein the resonance frequency is further evaluated for moisture content of the scanned fiber structure.

7. The method as in claim 1, wherein the calculated band mass is sent to a mechanism of a textile processing machine for processing the scanned fiber structure as a function of band mass.

8. The method as in claim 7, wherein the textile processing machine is a draw frame, and the band mass is used for regulating drawing of the fiber structure in the draw frame.

9. The method as in claim 7, wherein the textile processing machine is one of a regulated card, a card with a regulated drafting device, a combing machine with a regulated or unregulated drafting device, or a draw frame.

10. A method for determining band mass of a fiber structure conveyed through a spinning preparation machine having a drafting device with successive draw parts for drawing the fiber structure, said method comprising:
with a microwave sensor, coupling microwaves into a microwave resonator, the microwaves having a variable self resonance;
conveying the fiber structure through the microwave resonator at an inlet or an outlet of the drafting device such that the self resonance of the microwaves varies as a function of varying band mass and moisture of the conveyed fiber structure;
detecting the varied self resonance of the microwaves and evaluating for frequency detuning and damping of the varied self resonance frequency as a result of influencing the microwaves with the fiber structure;
calculating band mass of the scanned fiber structure from the frequency detuning and damping, the band mass calculation being adjusted for by moisture of the scanned fiber structure;
processing the fiber structure with the drafting device as a function of the calculated band mass; and
generating a signal when fluctuations in monitored band mass at the drafting device exceeds established threshold values, such that said signal is used to emit a warning signal or stop operation of the spinning preparation machine.

11. The method as in claim 10, further comprising detecting and evaluating the changed resonance frequency of the microwaves as a result of scanning the fiber structure having a particular band mass, as well as the half-width of the changed resonance frequency.

12. The method as in claim 10, further comprising:
supplying microwaves having at least two different frequencies to the resonator;
detecting shifts in the resonance frequency of the supplied microwaves by comparison of resonance curves of the resonator uninfluenced by a fiber structure with curves that are influenced by the presence of the scanned fiber structure; and detecting damping by comparison of the amplitudes of the resonance curves at the frequencies of the supplied microwaves.

13. A method for determining band mass of a fiber structure conveyed through a spinning preparation machine having a drafting device with successive draw parts for drawing the fiber structure, said method comprising:

with a microwave sensor, coupling microwaves into a microwave resonator, the microwaves having a variable self resonance;

conveying the fiber structure through the microwave resonator such that the self resonance of the microwaves varies as a function of varying band mass and moisture of the conveyed fiber structure;

detecting the varied self resonance of the microwaves and evaluating for frequency detuning, and damping of the varied self resonance frequency as a result of influencing the microwaves with the fiber structure;

calculating band mass of the scanned fiber structure from the frequency detuninq and damping, the band mass calculation being adjusted for by moisture of the scanned fiber structure;

processing the fiber structure with the drafting device as a function of the calculated band mass; and detecting breaks in the scanned fiber structure.

14. The method as in claim 10, wherein the calculated band mass is sent to a regulating unit configured with the draw parts of the drafting device for leveling out fluctuations in the sliver mass as a function of the calculated band mass.

15. The method as in claim 10, further comprising detecting temperature of the scanned fiber structure and adjusting the calculated band mass as a function of temperature.

16. A method for determining band mass of a fiber structure conveyed through a spinning preparation machine having a drafting device with successive draw parts for drawing the fiber structure, said method comprising:

with a microwave sensor, coupling microwaves into a microwave resonator, the microwaves having a variable self resonance;

conveying the fiber structure through the microwave resonator such that the self resonance of the microwaves varies as a function of varying band mass and moisture of the conveyed fiber structure;

detecting the varied self resonance of the microwaves and evaluating for frequency detuning, and damping of the varied self resonance frequency as a result of influencing the microwaves with the fiber structure;

calculating band mass of the scanned fiber structure from the frequency detuning and damping, the band mass calculation being adjusted for by moisture of the scanned fiber structure;

processing the fiber structure with the drafting device as a function of the calculated band mass; and wherein a rate of detection of the varied resonance frequency of the microwaves from the resonator is coordinated with a conveying speed of the fiber structure.

17. A method for determining band mass of a fiber structure conveyed through a spinning preparation machine having a drafting device with successive draw parts for drawing the fiber structure, said method comprising:

with a microwave sensor, coupling microwaves into a microwave resonator, the microwaves having a variable self resonance;

conveying the fiber structure through the microwave resonator such that the self resonance of the microwaves varies as a function of varying band mass and moisture of the conveyed fiber structure;

detecting the varied self resonance of the microwaves and evaluating for frequency detuning, and damping of the varied self resonance frequency as a result of influencing the microwaves with the fiber structure;

calculating band mass of the scanned fiber structure from the frequency detuning and damping, the band mass calculation being adjusted for by moisture of the scanned fiber structure;

processing the fiber structure with the drafting device as a function of the calculated band mass; and wherein a rate of detection of the varied resonance frequency of the microwaves from the resonator is set at a fixed scanning length of fiber structure.

18. A method for determining band mass of a fiber structure conveyed through a spinning preparation machine having a drafting device with successive draw parts for drawing the fiber structure, said method comprising:

with a microwave sensor, coupling microwaves into a microwave resonator, the microwaves having a variable self resonance;

conveying the fiber structure through the microwave resonator such that the self resonance of the microwaves varies as a function of varyinq band mass and moisture of the conveyed fiber structure;

detecting the varied self resonance of the microwaves and evaluating for frequency detuning, and damping of the varied self resonance frequency as a result of influencing the microwaves with the fiber structure;

calculating band mass of the scanned fiber structure from the frequency detuning and damping, the band mass calculation being adjusted for by moisture of the scanned fiber structure;

processing the fiber structure with the drafting device as a function of the calculated band mass; and wherein a rate of detection of the varied resonance frequency of the microwaves from the resonator is set at a fixed time interval that is a function of conveying speed of the fiber structure.

19. A method for determining band mass of a fiber structure conveyed through a spinning preparation machine having a drafting device with successive draw parts for drawing the fiber structure, said method comprising:

with a microwave sensor, coupling microwaves into a microwave resonator, the microwaves having a variable self resonance;

conveying the fiber structure through the microwave resonator such that the self resonance of the microwaves varies as a function of varying band mass and moisture of the conveyed fiber structure;

detecting the varied self resonance of the microwaves and evaluating for frequency detuning, and damping of the varied self resonance frequency as a result of influencing the microwaves with the fiber structure;

calculating band mass of the scanned fiber structure from the frequency detuninq and damping, the band mass calculation being adjusted for by moisture of the scanned fiber structure;

processing the fiber structure with the drafting device as a function of the calculated band mass; and wherein overlapping longitudinal sections of the fiber structure are successively scanned with the microwaves.

20. A method for determining band mass of a fiber structure conveyed through a spinning preparation machine having a drafting device with successive draw parts for drawing the fiber structure, said method comprising:
with a microwave sensor, coupling microwaves into a microwave resonator, the microwaves having a variable self resonance;
conveying the fiber structure through the microwave resonator such that the self resonance of the microwaves varies as a function of varying band mass and moisture of the conveyed fiber structure;
detecting the varied self resonance of the microwaves and evaluating for frequency detuning, and damping of the varied self resonance frequency as a result of influencing the microwaves with the fiber structure;
calculating band mass of the scanned fiber structure from the frequency detuning and damping, the band mass calculation being adjusted for by moisture of the scanned fiber structure;
processing the fiber structure with the drafting device as a function of the calculated band mass; and
generating or supplementing a spectrogram of the scanned fiber structure with measurements from the microwave sensor.

21. The method as in claim 10, wherein the fiber structure is conveyed substantially free from oscillations through the resonator.

22. The method as in claim 10, wherein the fiber structure is conveyed under tension through the resonator.

23. The method as in claim 10, wherein the fiber structure is conveyed with lateral guidance through the resonator.

24. The method as in claim 10, wherein the fiber structure is comprised of several fiber slivers conveyed adjacent to each other through the spinning preparation machine.

25. The method as in claim 24, wherein the several fiber slivers are conveyed through guide means before being conveyed through the resonator.

26. The method as in claim 25, wherein the several fiber slivers are compressed together by the guide means.

27. The method as in claim 24, wherein the several fiber slivers are conveyed in at least two groups through the resonator.

28. A method for determining band mass of a fiber structure conveyed through a spinning preparation machine having a drafting device with successive draw parts for drawing the fiber structure, said method comprising:
with a microwave sensor, coupling microwaves into a microwave resonator, the microwaves having a variable self resonance;
conveying the fiber structure through the microwave resonator such that the self resonance of the microwaves varies as a function of varying band mass and moisture of the conveyed fiber structure;
detecting the varied self resonance of the microwaves and evaluating for frequency detuning, and damping of the varied self resonance frequency as a result of influencing the microwaves with the fiber structure;
calculating band mass of the scanned fiber structure from the frequency detuninq and damping, the band mass calculation being adjusted for by moisture of the scanned fiber structure;
processing the fiber structure with the drafting device as a function of the calculated band mass; and
wherein the several fiber slivers are conveyed in at least two groups through the resonator and the groups of fiber slivers are conveyed toward each other after the resonator and conveyed substantially parallel to each other into the drafting device.

29. The method as in claim 24, wherein the several fiber slivers are maintained in relative position with respect to each other through the resonator and the drafting device.

30. A method for determining band mass of a fiber structure conveyed through a spinning preparation machine having a drafting device with successive draw parts for drawing the fiber structure, said method comprising:
with a microwave sensor, coupling microwaves into a microwave resonator, the microwaves having a variable self resonance;
conveying the fiber structure through the microwave resonator such that the self resonance of the microwaves varies as a function of varying band mass and moisture of the conveyed fiber structure;
detecting the varied self resonance of the microwaves and evaluating for frequency detuning, and damping of the varied self resonance frequency as a result of influencing the microwaves with the fiber structure;
calculating band mass of the scanned fiber structure from the frequency detuning and damping, the band mass calculation being adjusted for by moisture of the scanned fiber structure;
processing the fiber structure with the drafting device as a function of the calculated band mass; and
periodically cleaning the resonator with a pressurized or vacuum air source.

31. A textile fiber spinning preparation machine that processes a fiber structure as a function of band mass of the fiber structure conveyed through said machine, comprising:
a microwave sensor, said microwave sensor further comprising
a microwave generator configured to produce variable frequency microwaves;
a microwave resonator coupled with said microwave generator, said resonator including a specimen volume structure through which the fiber is conveyed;
a microwave detector disposed to detect microwaves coupled out of said resonator;
an evaluation unit in communication with said detector and configured to evaluate microwave resonance signals to calculate band mass of the fiber structure from said resonance signals, said evaluation unit compensating said calculated band mass as a function of fiber structure moisture; and
wherein said microwave generator supplies microwaves having at least two differing frequencies to said resonator, and said evaluation unit comprises circuitry that detects resonance frequency shifts of the microwaves by comparing resonance curves influenced by the scanned fiber structure with resonance curves of uninfluenced microwaves in said resonator, said evaluation unit detecting damping by comparing amplitudes of the influenced resonance curves with the resonance curves not influenced by the fiber structure.

32. The machine as in claim 31, wherein said microwave sensor is operatively disposed at an inlet to said spinning preparation machine.

33. The machine as in claim 31, wherein said microwave sensor is operatively disposed at an outlet to said spinning preparation machine.

34. The machine as in claim 31, further comprising a drafting device and a regulating unit that controls drafting of the fiber structure through said drafting device, said evaluation unit in communication with said regulating unit such that drafting is controlled as a function of the calculated band mass of the fiber structure.

35. The machine as in claim 31, wherein several fiber slivers are guided adjacent and parallel to each other through said microwave sensor.

36. A textile fiber spinning preparation machine that processes a fiber structure as a function of band mass of the fiber structure conveyed through said machine, comprising:
a microwave sensor, said microwave sensor further comprising
a microwave generator configured to produce variable frequency microwaves;
a microwave resonator coupled with said microwave generator, said resonator including a specimen volume structure through which the fiber is conveyed;
a microwave detector disposed to detect microwaves coupled out of said resonator; and
an evaluation unit in communication with said detector and configured to evaluate microwave resonance signals to calculate band mass of the fiber structure from said resonance signals, said evaluation unit compensating said calculated band mass as a function of fiber structure moisture; and
guide elements disposed at an inlet and an outlet of said microwave sensor for conveying the fiber structure under tension through said microwave sensor.

37. The machine as in claim 36, wherein said guide elements comprise rotating roller pairs between which the fiber structure is clamped.

38. The machine as in claim 31, further comprising a compressive guide element disposed at an inlet of said microwave resonator, said compressive guide element compressing the fiber structure prior to scanning thereof in said resonator.

39. The machine as in claim 38, wherein said compressive guide element comprises guide surfaces rising generally transversely from a running path of the fiber structure.

40. The machine as in claim 39, wherein said compressive guide element comprises a double cone structure having tips facing and merging into each other.

41. The machine as in claim 38, wherein said compressive guide element comprises a pressure rod disposed at an inlet to said resonator.

42. A textile fiber spinning preparation machine that processes a fiber structure as a function of band mass of the fiber structure conveyed through said machine, comprising:
a microwave sensor, said microwave sensor further comprising
a microwave generator configured to produce variable frequency microwaves;
a microwave resonator coupled with said microwave generator, said resonator including a specimen volume structure through which the fiber is conveyed;
a microwave detector disposed to detect microwaves coupled out of said resonator; and
an evaluation unit in communication with said detector and configured to evaluate microwave resonance signals to calculate band mass of the fiber structure from said resonance signals, said evaluation unit compensating said calculated band mass as a function of fiber structure moisture; and
a drafting device for drafting the fiber structure as a function of the calculated band mass, the fiber structure defined by a plurality of adjacently conveyed fiber slivers, and deflection elements disposed between said microwave sensor and said drafting device such that the fiber slivers maintain substantially the same relative position with respect to each other from said microwave sensor to said drafting device.

43. The machine as in claim 42, wherein said deflection elements are staggered in the longitudinal and transverse direction with respect to a conveying path of the fiber slivers.

44. The machine as in claim 43, wherein at least one of said deflection elements are rotatable.

45. The machine as in claim 31, wherein said specimen volume structure in contact with the fiber structure is formed of a wear resistant material.

46. A textile fiber spinning preparation machine that processes a fiber structure as a function of band mass of the fiber structure conveyed through said machine, comprising:
a microwave sensor, said microwave sensor further comprising
a microwave generator configured to produce variable frequency microwave;
a microwave resonator coupled with said microwave generator, said resonator including a specimen volume structure through which the fiber is conveyed;
a microwave detector disposed to detect microwaves coupled out of said resonator; and
an evaluation unit in communication with said detector and configured to evaluate microwave resonance signals to calculate band mass of the fiber structure from said resonance signals, said evaluation unit compensating said calculated band mass as a function of fiber structure moisture; and
wherein said specimen volume structure is movable to various operating positions.

47. The machine as in claim 31, wherein said machine is one of a regulated card, a card with a regulated drafting device, a combing machine with a regulated or unregulated drafting device, or a draw frame.

48. The machine as in claim 31, wherein said machine is one of a card or a combing machine with a regulated drafting device module configured at an outlet thereof, said drafting device module controlled as a function of the calculated band mass conveyed through said machine.

49. The machine as in claim 31, wherein said machine is a card, said microwave sensor disposed at an outlet of said card.

50. A method for detecting foreign matter in a fiber structure conveyed through a textile spinning machine, comprising subjecting the fiber structure to microwaves such that a characteristic change of the microwaves is induced by the fiber structure, and detecting and processing the changed microwave characteristic to detect the presence of foreign matter in the fiber structure.

51. The method as in claim 50, comprising
with a microwave sensor, coupling microwaves into a microwave resonator, the microwaves having a variable self resonance;
conveying the fiber structure through the microwave resonator such that the self resonance of the microwaves varies as a function of varying band mass and moisture of the conveyed fiber structure, varying band mass of the fiber structure caused at least in part by the presence of foreign matter in the fiber structure;
detecting the varied self resonance of the microwaves and evaluating for frequency, detuning, and damping of the varied self resonance frequency as a result of influencing the microwaves with the fiber structure;
calculating band mass of the scanned fiber structure from the frequency, detuning and damping, the band mass calculation being adjusted for by moisture of the scanned fiber structure; and determining the presence of foreign matter in the fiber structure by comparing deviations in band mass to stored data correlating band mass values to particular types of foreign matter.

52. A textile spinning preparation machine configured for carrying out the method of claim 51.

53. The method as in claim 16, wherein the conveying speed is at least one of a run-in speed of the fiber structure running into the spinning preparation machine or a delivery speed of the fiber structure leaving the spinning preparation machine.

* * * * *